US00PP11569P

United States Patent [19]

Pieters

[11] Patent Number: Plant 11,569

[45] Date of Patent: Oct. 17, 2000

[54] CHRYSANTHEMUM PLANT NAMED 'GEDI ORO8'

[76] Inventor: Dirk Pieters, Schierveldestraat 3A, Oosnieuwkerke, 8840 Staden, Belgium

[21] Appl. No.: 09/168,914

[22] Filed: Oct. 8, 1998

[51] Int. Cl.[7] ..... A01H 5/00

[52] U.S. Cl. ..... Plt./290; Plt./296

[58] Field of Search ..... Plt./290, 296, 295

[56] References Cited

U.S. PATENT DOCUMENTS

P.P. 10,419 5/1998 Pieters ..... Plt./287

*Primary Examiner*—Howard J. Locker

*Attorney, Agent, or Firm*—Christie, Parker & Hale, LLP

[57] ABSTRACT

A new plant variety of chrysanthemum producing large, orange flowers having slight yellow tone in center.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'GEDI ORO8'.

The new variety is a natural whole plant mutation discovered in a controlled planting of the variety 'Ozenda' U.S. Plant Pat. No. 10,419 in Staden, Belgium. The new variety has been asexually reproduced by vegetative cuttings in Ventura County, Calif. and the distinguishing characteristics are retained through successive generations of asexual reproduction.

SUMMARY OF THE INVENTION

'GEDI ORO8' produces orange decorative flowers with a slight yellow tone in center.

COMPARISON WITH PARENTS

'GEDI ORO8' differs from its parent in producing orange flowers whereas 'Ozenda' produces light lavender flowers.

BRIEF DESCRIPTION OF ILLUSTRATION

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. in the month of July. 'GEDI ORO8' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once with center buds removed about ten days after planting. It has been observed that longevity of individual blooms of 'GEDI ORO8' is about 18 days and the response time is about 7 weeks. No growth retardant was used on plants described. Useful growing conditions include night temperatures of about 18°–20° C. and day temperatures of about 20°–30° C. Natural season response in U.S. West Coast conditions is early October.

Plant:

*Habit.*—Mounding, herbaceous perennial, free branching.

*Height.*—About 28 cm.

*Number of breaks from pinch.*—About 4 to 5.

*Length of lateral branches.*—About 20 cm.

*Stem color.*—About 137B.

Foliage:

*Leaf arrangement.*—Alternate.

*Number of leaves per lateral branch.*—About 15 fully expanded leaves.

*Leaf size.*—Length: About 4.8 cm. Width: About 3.2 cm.

*Leaf shape.*—Ovate.

*Attachment.*—Petioled.

*Leaf apex.*—Acute.

*Base.*—Tapered.

*Margin.*—Palmately lobed.

*Aspect.*—Slightly undulate.

*Surface.*—Top: Pubescent. Bottom: Pubescent.

*Venation Color.*—Upperside: Near 146B. Underside: Near 138A.

*Petiole.*—Length: About 1.3 cm. Color: Near 146B.

*Color.*—Mature leaf: Top: Near 137A. Bottom: Near 137D. Young leaf: Top: Near 137A. Bottom: Near 138A.

Bloom:

*Inflorescence form.*—Cyme.

*Flower form.*—Decorative type inflorescence with slight open center.

*Number of blooms per branch.*—About 17.

*Diameter of fully expanded bloom.*—About 4.4 cm.

*Depth of fully expanded bloom.*—About 2.1 cm.

*Sepal number.*—About 25.Color: Near 137B. Length: About 0.6 cm. Width: About 0.3 cm.

*Peduncle.*—Length: Terminal: About 4 cm. Lateral: About 8 cm. Aspect: Slightly undulating, weak. Surface: Pubescent. Color: Near 138D.

*Flower Bud (when just showing color).*—Color: Near 168A. Diameter: Near 0.8 cm. Height: About 0.6 cm. Shape: Flattened sphere.

*Ray florets.*—Number per flower: About 130. Texture: Matte. Shape: Oblanceolate. Apex: 2 to 3 irregular obtuse lobes. Base: Tapered. Margin: Entire. Aspect: Recurved. Length: About 1.9 cm. Width: About 0.9 cm.

*Disc florets.*—Number per flower: About 60. Texture: Shiny. Shape: Cylindric, fluted apex. Length: About 0.6 cm. Width: About 0.1 cm.

*Fragrance.*—Faint.

Flower color:

*General flower description.*—Orange/bronze decorative.

*Ray florets, top side.*—Immature: Near 34B. Mature: Near 169B. Fading: Near 169D.

*Ray floret, under side.*—Immature: Near 26A. Mature: Near 26A. Fading: Near 26B.

*Disc florets.*—Immature: Near 7C. Mature: Near 16A. Fading: Near 20A.

*Changes as the flower ages.*—Color fades slightly.

Reproductive organs:

*Ray florets.*—Pistillate. Stigma shape: 2 forked. Stigma color: Near 12A. Style length: About 0.4 cm. Style color: Near 154D.

*Disc florets.*—Stigma shape: Linear. Stigma color: Near 7B. Style Length: About 0.3 cm. Style color: Near 154D. Stamen number: About 5. Anther length: About 0.2 cm. Pollen color: Near 14A. Pollen quantity: Moderate.

What is claimed is:

1. A new and distinct chrysanthemum plant of the variety substantially as herein shown and described.

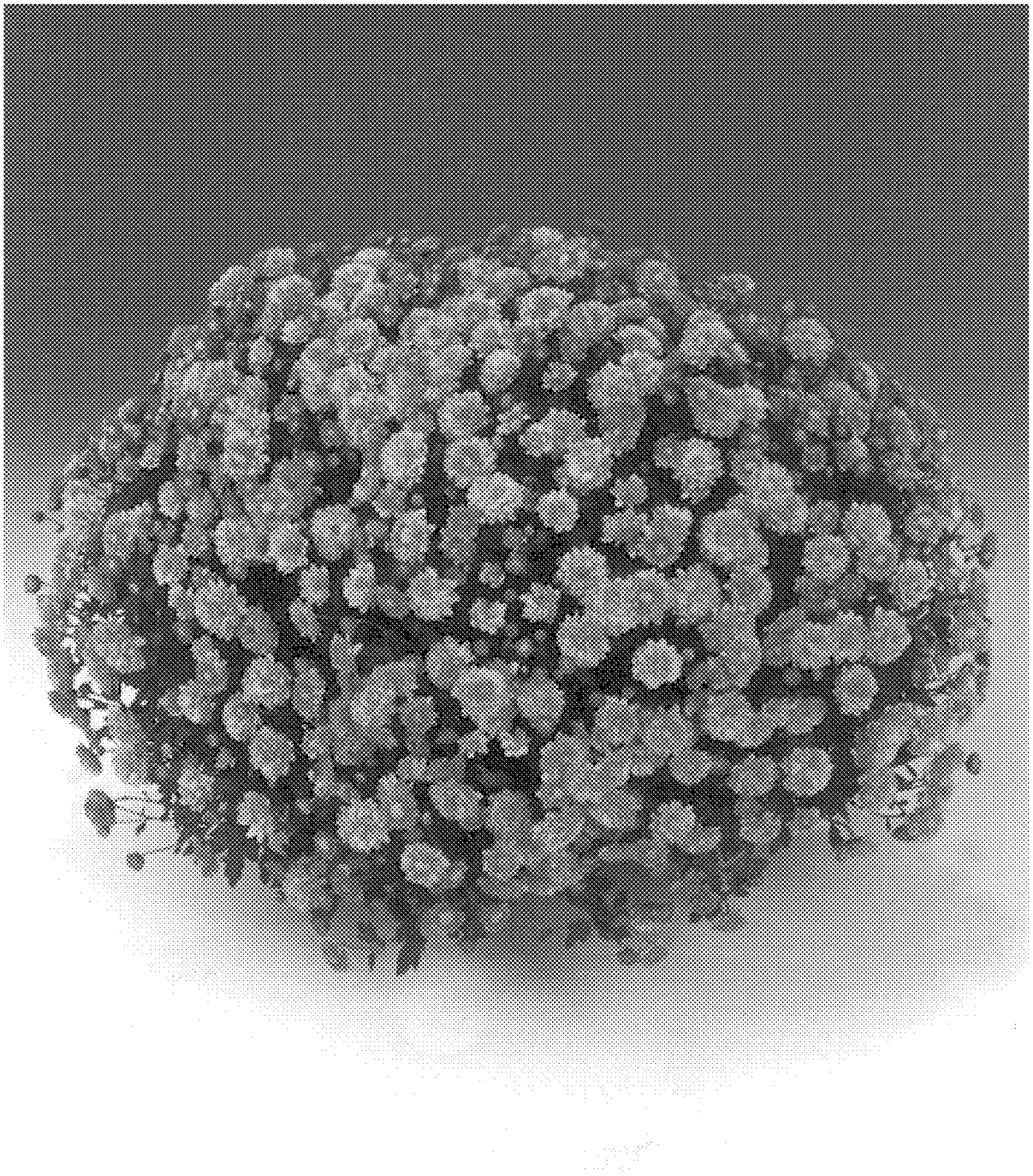

* * * * *